(12) United States Patent
Kim

(10) Patent No.: US 12,329,541 B2
(45) Date of Patent: Jun. 17, 2025

(54) BREAST IMPLANT AND APPARATUS FOR SENSING ABNORMALITY OF THE SAME

(71) Applicant: W. AI CO., LTD, Seoul (KR)

(72) Inventor: Jae Hong Kim, Seoul (KR)

(73) Assignee: W. AI CO., LTD., Seoul (KR)

( * ) Notice: Subject to any disclaimer, the term of this patent is extended or adjusted under 35 U.S.C. 154(b) by 622 days.

(21) Appl. No.: 17/671,357

(22) Filed: Feb. 14, 2022

(65) Prior Publication Data

US 2022/0265215 A1    Aug. 25, 2022

Related U.S. Application Data

(63) Continuation of application No. PCT/KR2021/013546, filed on Oct. 3, 2021.

(30) Foreign Application Priority Data

Feb. 21, 2021  (KR) .......................... 10-2021-0022995
Apr. 17, 2021  (KR) .......................... 10-2021-0050179

(51) Int. Cl.
  *A61F 2/12*   (2006.01)
  *A61B 5/00*   (2006.01)
  *A61L 27/52*  (2006.01)

(52) U.S. Cl.
  CPC ............ *A61B 5/686* (2013.01); *A61B 5/0022* (2013.01); *A61B 5/746* (2013.01); *A61F 2/12* (2013.01); *A61L 27/52* (2013.01); *A61B 2562/0247* (2013.01); *A61F 2250/0003* (2013.01)

(58) Field of Classification Search
  CPC ...... A61F 2/12; A61F 2250/0003; A61B 5/03; A61B 2562/164; A61B 5/686; A61B 2017/00796; A61B 2562/166; A61B 5/4851; A61K 8/042; A61N 1/05; A61N 1/00; Y10S 524/916
  See application file for complete search history.

(56) References Cited

U.S. PATENT DOCUMENTS

2009/0012372 A1  1/2009  Burnett et al.
2018/0085210 A1  3/2018  Govari et al.

FOREIGN PATENT DOCUMENTS

JP   2010-534551 A   11/2010
KR   10-1235284 B1   2/2013
KR   10-1966979 B1   8/2019

*Primary Examiner* — Deborah L Malamud
(74) *Attorney, Agent, or Firm* — Umberg Zipser LLP

(57) ABSTRACT

This application relates to a breast implant and an apparatus for sensing an abnormality of the breast implant. In one aspect, the breast implant includes a shell including an injection hole and forming an outer cover of the breast implant and a filler of a gel state injected into the shell through the injection hole. The breast implant may also include a first patch configured to seal the injection hole, the first patch including a first sensor module. The breast implant may further include a second patch configured to be attached on at least one of a second position facing the first position and a third position to which a pressure due to a gravity is applied when the breast implant is inserted in a breast and a body is kept upright without an external pressure applied, the second patch including a second sensor module.

10 Claims, 13 Drawing Sheets

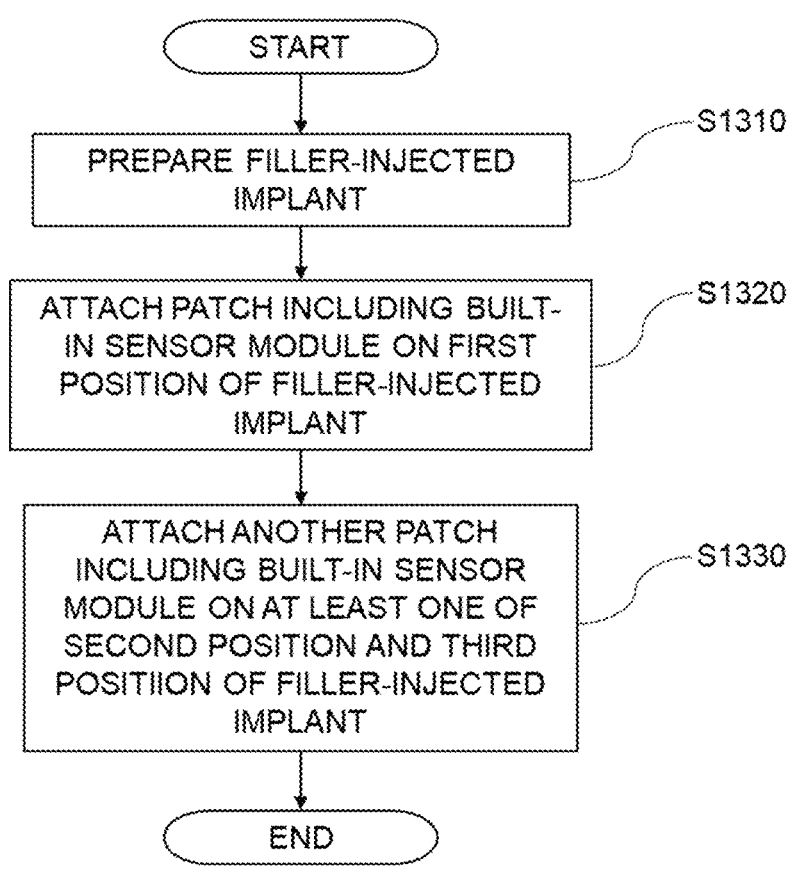

BREAST IMPLANT AND APPARATUS FOR SENSING ABNORMALITY OF THE SAME

CROSS-REFERENCE TO RELATED APPLICATIONS

This application is a continuation of International Application No. PCT/KR2021/013546, filed Oct. 3, 2021, which is based upon and claims the benefit of priority from Korean Patent Application No. 10-2021-0022995 filed Feb. 21, 2021 and Korean Patent Application No. 10-2021-0050179 filed Apr. 17, 2021, which is now Korean Patent No. 10-2324101, the contents of which are incorporated herein by reference in their entirety.

BACKGROUND

Technical Field

The present disclosure relates to a breast implant and an apparatus for sensing an abnormality of the breast implant.

Description of the Related Technology

A breast with beauty and volume is the shared wishes of most women. The breast implant is one of the easiest and most effective methods to realize the wishes of such women.

The breast reconstruction employing the breast implant is a method of securing a space for inserting the breast implant in a breast and increasing the volume of the breast by inserting the breast implant in the secured space.

SUMMARY

According to some embodiments of the present disclosure, a breast implant includes a shell including an injection hole and forming an outer cover of the breast implant, a filler of a gel state injected into the shell through the injection hole, a first patch configured to seal the injection hole, the first patch including a first sensor module, and a second patch configured to be attached on at least one of a second position facing the first position and a third position to which a pressure due to a gravity is applied when the breast implant is inserted in a breast and a body is kept upright without an external pressure applied, the second patch including a second sensor module.

According to some embodiments of the present disclosure, an apparatus for sensing an abnormality of a breast implant includes a wireless power transmitting unit configured to transmit a power in a wireless manner, an abnormality sensing unit configured to receive a pressure signal from at least one of the first sensor module and the second sensor module of the breast implant according to some embodiments of the present disclosure and to sense an abnormality of the breast implant based on the pressure signal, and an alarm generating unit configured to, upon the abnormality sensing unit sensing the abnormality of the breast implant, generate an alarm.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIGS. 10 to 13 are flowcharts for explaining a method of manufacturing a breast implant according to some embodiments of the present disclosure.

DETAILED DESCRIPTION

Figure 1:
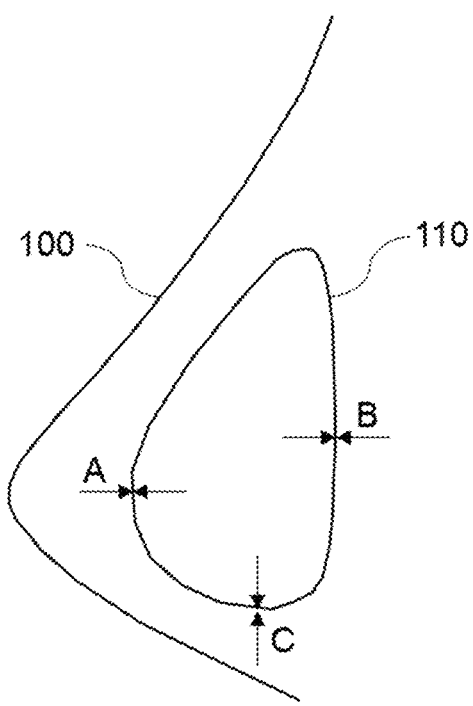
FIG. 1 is a schematic diagram for explaining pressures applied to a breast implant inserted in a breast in some embodiments of the present disclosure.

Breast implants are generally manufactured using a cohesive gel that is a silicone having a high cohesive force. The cohesive gel has an advantage in that an outer cover (shell) is strong and a shape is naturally formed after a surgery, remedying disadvantages of a conventional silicone gel (see, for example, Korean Pat. No. 10-1235284, Korean Pat. No. 10-1966979, and Japanese Pat. Laid-Open No. 2010-534551).

Popular side effects seen after a surgery for reconstructing a breast with a breast implant include rupture and capsular contracture.

When a rupture is generated and a silicone component is remained in the body for a long time, the silicone component may permeate through the breast tissue, possibly causing a breast feeding hard and a difficulty in a breast cancer examination. Sometimes the silicone penetrates into a lymph node due to the rupture of the breast implant, and in this case, the penetrated silicone may be incompletely removed and a lymphedema after removing the silicone or a spreading of the silicone to the whole body may occur.

The capsular contracture is a phenomenon generated from thickening of a capsule newly formed surrounding a breast implant, which is generated within the first two years after a surgery, which is one of the most popular side effects.

A capsular contracture causes deformation and pain, and in a worse case, a reoperation is needed to remove the breast implant and to remove the capsule.

In order to examine the two representative side effects after inserting the breast implant, a patient needs to visit a hospital to consult a doctor and to carry out an image medical inspection such as an ultrasound and an MRI.

Even without a particular symptom, it is recommended to carry out an ultrasound examination every year after inserting the breast implant.

Exemplary embodiments of the present disclosure are described in detail below with reference to the accompanying drawings.

It is an object of the present disclosure to provide a breast implant with which an abnormality of the breast implant can be effectively sensed after inserting the breast implant in a breast.

It is an object of the present disclosure to provide an apparatus for sensing an abnormality of a breast implant, which can effectively sense an abnormality of the breast implant after inserting the breast implant in a breast.

The challenges to be addressed by the present disclosure are not limited to those mentioned above, and other unmentioned problems can be clearly understood by those skilled in the art from the following description.

A breast implant according to some embodiments of the present disclosure is manufactured with, for example, a silicone material and is used for a plastic surgery of a breast, a hip, or the like, which is inserted in a body and forms and maintains a consistent shape in the body.

Although a breast implant for reconstructing a breast is explained as an example in the present specification, the breast implant and the apparatus for sensing an abnormality of a breast implant according to some embodiments of the present disclosure can be applied to most implants including a shell and a gel-type filler and being inserted in a body for a specific purpose.

FIG. 1 is a schematic diagram for explaining pressures applied to a breast implant inserted in a breast in some embodiments of the present disclosure.

A breast implant for reconstructing a breast is explained as an example in FIG. 1. A plastic surgery of a breast employing a breast implant is a method of securing a space for inserting the breast implant in a breast and increasing the volume of the breast by inserting the breast implant in the secured space.

As shown in FIG. 1, when a breast implant 110 is inserted in a breast 100, in a normal state in which no external pressure is applied on the breast 100, a pressure A is applied on the breast implant 110 from outside a body, a pressure B is applied on the breast implant 110 from or against inside the body, and pressure C is applied on the breast implant 110 due to the gravity.

Typically, a silicone gel is inserted in the shell of the breast implant 110. The breast implant 110 is sealed by a patch at a position on the bottom of the breast implant 110 (near a position indicated by B) in a manner that consistent tension is maintained. However, when a part of the breast implant 110 is ruptured or a capsular contracture is generated at a part of the breast implant 110, at least one of the pressures A, B, and C is changed.

In the case of the cohesive-gel implant, which is widely used in these days, even if a part of the breast implant 110 is ruptured after inserting the breast implant 110 in the breast 100, a patient can hardly feel an abnormality, which is referred to as a silent rupture. That is, the cohesive gel keeps the gel state even when the breast implant 110 is ruptured.

An image inspection by a magnetic resonance imaging (MRI) is so far one of the most precise methods to inspect a rupture of the breast implant 110. However, the MRI itself still shows a false positive and a false negative and can be a burden to a patient in terms of the cost.

When a foreign material comes into a body, a capsule is formed around the foreign material. Such capsule excessively formed and hardened causes a capsular contracture.

When a breast implant is inserted in a breast, the blood platelet in the blood is activated and a material called the transforming growth factor β (TGF-β) is secreted. The TGF-β takes a role of gathering monocytes around the breast implant where an inflammation is generated. The monocyte is a sort of the white blood cell, which develops into a macrophage near the inflammation and secretes the TGF-β again. This results in a fibroblast near the inflammation and a collagen synthesized from the fibroblast generates the capsular contracture.

Figure 2:
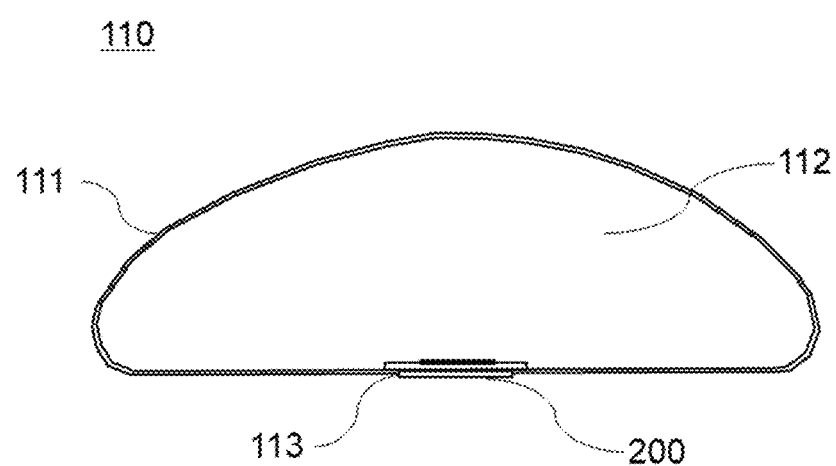
FIG. 2 is a schematic diagram of a breast implant according to some embodiments of the present disclosure.

FIG. 2 is a schematic diagram of the breast implant 110 according to some embodiments of the present disclosure.

As shown in FIG. 2, the breast implant 110 according to some embodiments of the present disclosure includes a shell 111 forming an outer cover of teardrop type or round type, a silicone gel 112 as a filler injected into the shell 111, and a patch 200 for sealing an injection hole 113 for injecting the silicone gel 112.

The patch 200 according to some embodiments of the present disclosure includes a sensor module 300 including a pressure sensor for sensing a pressure applied to the breast implant 110.

Figure 3:
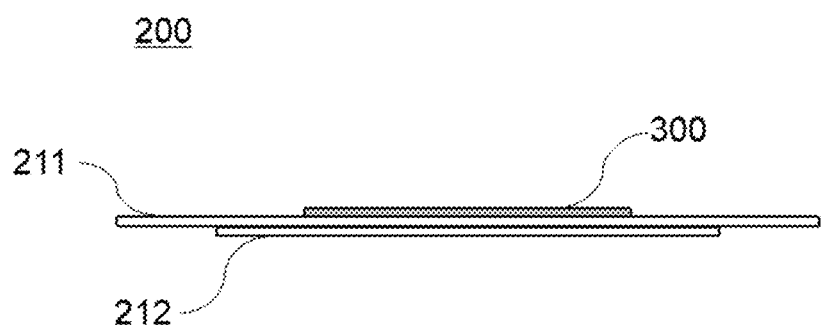
FIGS. 3 and 4 are schematic diagrams of a patch including a sensor module according to some embodiments of the present disclosure.
Figure 4:
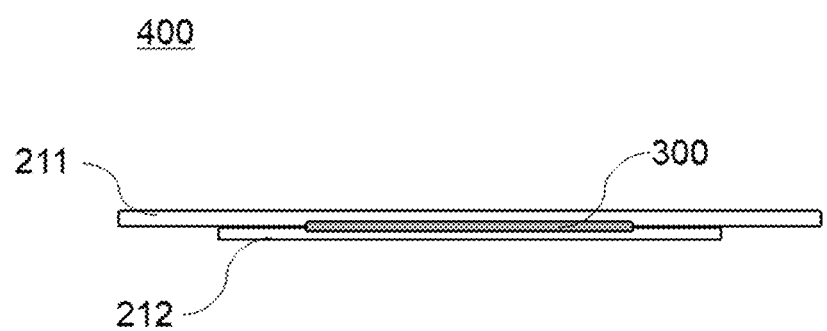

FIG. 3 is a schematic diagram of the patch 200 including a sensor module 300 according to some embodiments of the present disclosure. FIG. 4 is a schematic diagram of a patch 400 including the sensor module 300 according to some embodiments of the present disclosure.

The patch 200 shown in FIG. 3 includes a first barrier (inner barrier) 211 forming a first side facing inside the breast implant 110 upon being attached on the breast implant 110 with the filler of the gel state injected, a second barrier (outer barrier) 212 facing the first barrier 211 and forming a second side opposite to the first side. The sensor module 300 is disposed on the first side of the first barrier 211.

In the patch 400 shown in FIG. 4, the sensor module 300 is disposed between the first barrier 211 and the second barrier 212.

The patch 200, 400 is a unit member formed by the first barrier 211 and the second barrier 212 making contact with each other. The first barrier 211 forms the inner side of the patch 200, 400, and the second barrier 212 forms the outer side of the patch 200, 400.

Therefore, the patch 200 shown in FIG. 3 can be manufactured by forming a unit member with the first barrier 211 and the second barrier 212 having contact with each other and then attaching the sensor module 300 on a part of the outer surface of the first barrier 211.

The patch 400 can be manufactured by sandwiching the sensor module 300 between the first barrier 211 and the second barrier 212.

Figure 5:
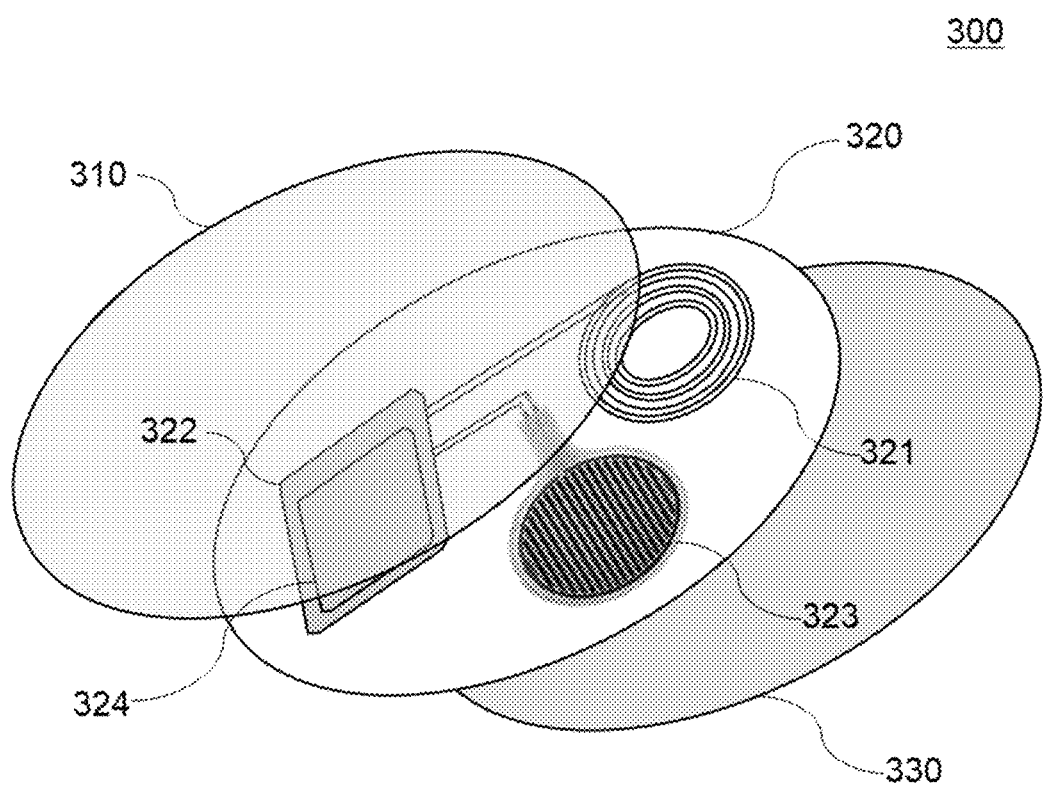
FIG. 5 is an exploded view of a sensor module according to some embodiments of the present disclosure.

FIG. 5 is an exploded view of the sensor module 300 according to some embodiments of the present disclosure.

As shown in FIG. 5, the sensor module 300 is formed as a film including two protective films 310, 330 and a substrate 320 between the two protective films 310, 330. On the substrate 320, at least one pressure sensor 323 for sensing a pressure applied on the breast implant and outputting a pressure signal, a controller 322 for transmitting the pressure signal from the pressure sensor 323 to the outside, and a wireless power receiving unit 321 for receiving a power from the outside and providing the power to the controller 322.

The pressure sensor 323 is an element that, when a predetermined pressure or force is applied, generates a signal proportional to the pressure or the force applied. The pressure sensor 323 includes a diaphragm sensor that curves according to the pressure or the force applied, a force sensing resistor (FSR) including two conductive plate and a conductive polymer between the two conductive plate, and a piezoelectric element that generates a voltage when a pressure is applied.

Although a tension sensor that senses a tension of the shell of the breast implant can be used instead of the pressure sensor, as a change of the tension is also a physical amount proportional to a change of the pressure due to the rupture or the capsular contracture of the breast implant, the tension sensor is considered as a type of the pressure sensor in the present specification.

In some embodiments of the present disclosure, the sensor module 300 further includes a battery 324 for storing the power received by the wireless power receiving unit 321 in a wireless manner.

That is, the sensor module 300 according to some embodiments of the present disclosure can operate either by receiving the power in a wireless manner only without a battery or by charging a battery with the power received in a wireless manner.

Figure 6:
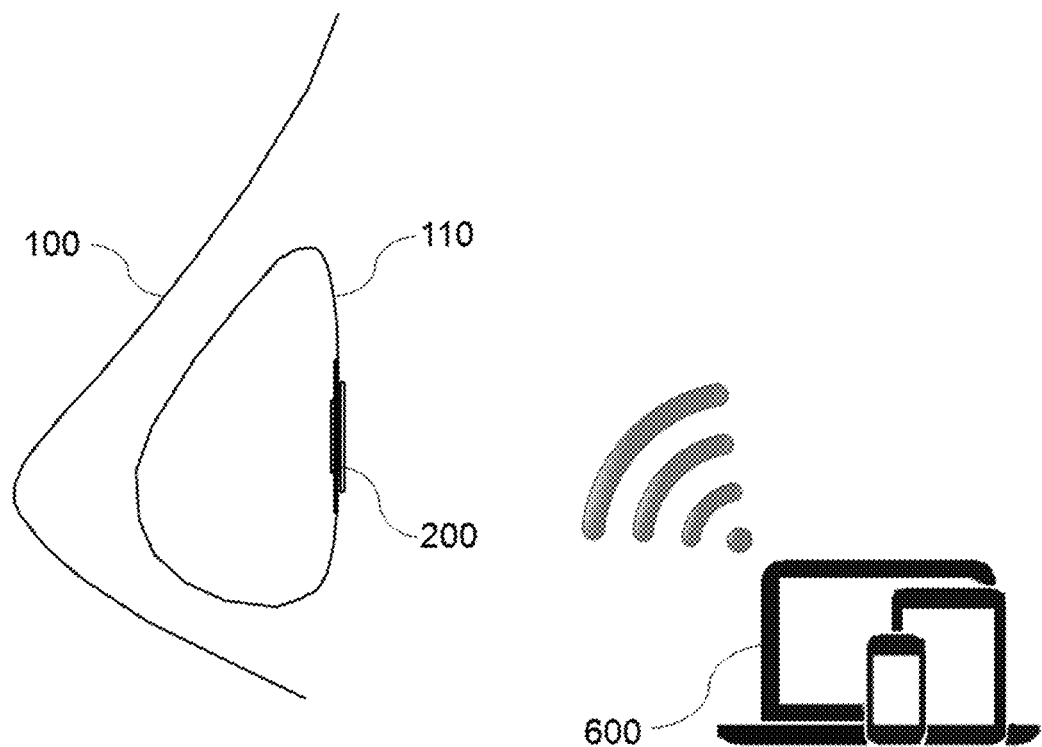
FIGS. 6 and 7 are schematic diagrams of an apparatus for sensing an abnormality of a breast implant according to some embodiments of the present disclosure.
Figure 7:
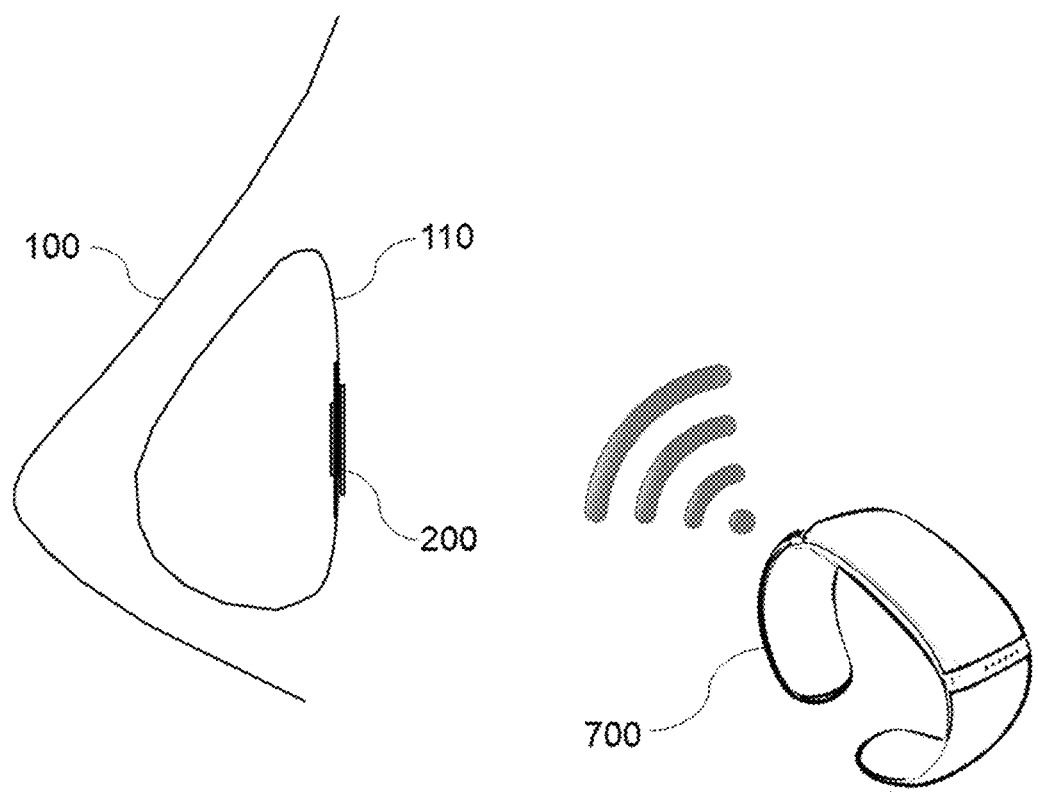

FIGS. 6 and 7 are schematic diagrams of an apparatus for sensing an abnormality of a breast implant according to some embodiments of the present disclosure.

The breast implant according to some embodiments of the present disclosure includes, as shown in FIG. 2, the shell 111 of the silicone material, the silicone gel 112 filled in the shell 111, and at least one patch 200, 400.

An apparatus 600 for sensing an abnormality of a breast implant shown in FIG. 6 transmits the power to the sensor module 300 of the breast implant, receives the pressure signal from the sensor module 300, determines the abnormality of the breast implant based on the pressure signal, and outputs a result of determination upon determining the abnormality.

The apparatus 600 includes a computing device including a computer and a digital pad such as a personal digital assistant (PDA) and a smart phone, having functions of the wireless communication and the wireless power transmission.

An apparatus 700 for sensing an abnormality of a breast implant shown in FIG. 7 has a form of a smart watch that is wearable. The apparatus 700 transmits the power to the sensor module 300 of the breast implant, receives the pressure signal from the sensor module 300, determines the abnormality of the breast implant based on the pressure signal, and outputs a result of determination upon determining the abnormality.

In some embodiments of the present disclosure, the apparatus 600, 700 stores, in a memory (not shown), an initial pressure sensed by the sensor module 300 when the breast implant 110 is inserted in the body, compares the pressure indicated by the pressure signal received from the sensor module 300 with the initial pressure, and senses the abnormality of the breast implant 110 based on a result of comparison.

That is, when there is a change in the pressure due to the rupture or the capsular contracture, a user is notified of the rupture or the capsular contracture of the breast implant according to the change of the pressure, to enable the user to take a proper action at the right time.

This can help the user to remove an anxiety about maintaining the breast with safety for a long time after inserting the breast implant in the breast, and at the same time, to relieve an inconvenience of taking an ultrasound inspection or an MRI inspection on a regular basis.

Figure 8:
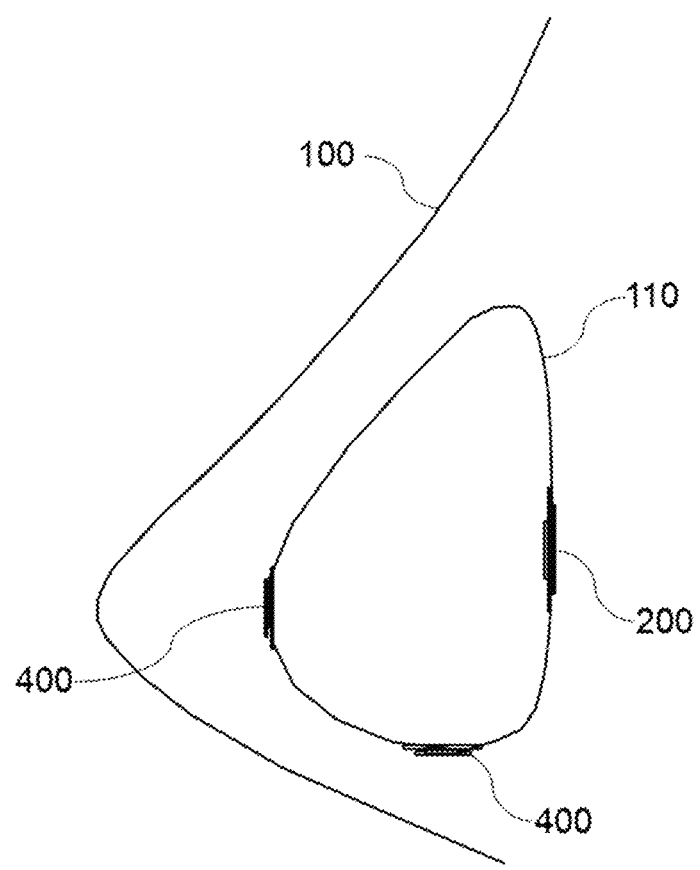
FIG. 8 is a schematic diagram showing an example of attaching a patch including a sensor module according to some embodiments of the present disclosure.

FIG. 8 is a schematic diagram showing an example of attaching a patch 200 and a patch 400 each including a sensor module according to some embodiments of the present disclosure.

As shown in FIG. 1, when a breast implant is inserted in a breast, in a normal state in which no external pressure is applied on the breast, a pressure A is applied on the breast implant 110 from outside a body, a pressure B is applied on the breast implant 110 from or against inside the body, and pressure C is applied on the breast implant 110 due to the gravity.

Therefore, by disposing the patch 200, 400 on at least one of positions A, B, and C, it is possible to sense the change of the pressure when there is an abnormality in the breast implant and to notify the user of the abnormality.

As shown in FIG. 8, the patch 200 including the sensor module 300 on the surface of the first barrier 211 or the patch 400 including the sensor module 300 between the first barrier 211 and the second barrier 212 can be attached on the position B, and the patch 400 can be attached on the positions A and C not to allow the sensor module 300 to make direct contact with the skin tissue.

As shown in FIGS. 1 and 8, the position B may not show a large change of the pressure due to an abnormality of the breast implant as a fixed wall is formed against the body and the sensor module 300 of the patch 200 disposed at this position senses the pressure exerted on a large area forming the bottom of the breast implant 110.

On the other hand, in the case of the position A or the position C, as a fluidity is relatively large compared to the position B, the change of the pressure due to the abnormality of the breast implant can be relatively large.

When an abnormality of the breast implant is sensed and, for example, it is determined that a rupture of the breast implant is sensed, the breast implant inserted in the breast is removed and a new breast implant is inserted in the breast again. Therefore, an error in the determination of the abnormality can cause a considerably negative consequence.

In order to prevent such errors in the determination of the abnormality, in some embodiments of the present disclosure, a first patch (patch 200) and a second patch (patch 400) are attached on at least two positions among the position B (first position), the position A (second position), and the position C (third position) to minimize the error in the determination of the abnormality due to the relative magnitude of the change in the pressure.

In some embodiments of the present disclosure, the second patch (patch 400) attached on the position A (second position) and the position C (third position) is smaller than the first patch (patch 200) attached on the position B (first position) in diameter.

This is because, as shown in FIG. 8, the position A (second position) and the position C (third position) have smaller areas flat enough to dispose the patch compared to the position B (first position).

For the same reason, the second patch (patch 400) attached on the position C (third position) can have a diameter smaller than that of the second patch (patch 400) attached on the position A (second position).

In some embodiments of the present disclosure, the apparatus 600, 700 stores the initial pressure for each of a plurality of positions, for example, the positions A, B, and C shown in FIG. 1 in the memory.

The apparatus 600, 700 may output an abnormality of the breast implant when a difference between the pressure indicated by at least one of the pressure signals received from the sensor modules 300 disposed at the plurality of positions and the initial pressure stored in the memory in association with the corresponding position exceeds a predetermined threshold.

In some embodiments of the present disclosure, the apparatus 600, 700 sets a threshold for determining an abnormality in a pressure signal received from one sensor module 300 larger than thresholds for determining an abnormality in pressure signals received from the other sensor modules 300. By configuring the apparatus 600, 700 in this manner, it is possible to determine the abnormality with the pressure signal from the one sensor module when the degree of the abnormality is considerable and to determine no abnormality when the degree of the abnormality is trivial and an abnormality in one sensor module is permissible, which can avoid an unnecessary alarming of the abnormality.

In some embodiments of the present disclosure, the apparatus 600, 700 sets different thresholds for a plurality of sensor modules from each other to determine the abnormality. For example, the apparatus 600, 700 sets the threshold for the sensor module on the bottom of the breast implant (position C in FIG. 1) larger or smaller than the thresholds for the sensor modules on the other positions. By configuring the apparatus 600, 700 in this manner, it is possible to make a proper determination considering the change in the pressure depending on the position of the breast implant.

Figure 9:
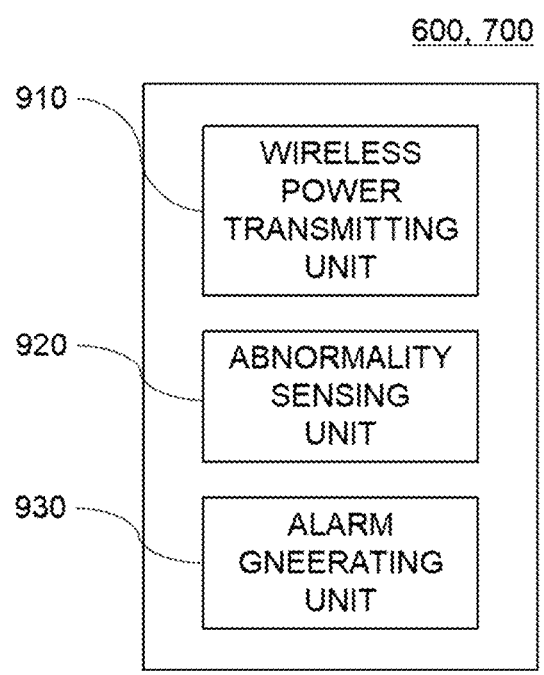
FIG. 9 is a functional block diagram of an apparatus for sensing an abnormality of a breast implant according to some embodiments of the present disclosure.

FIG. 9 is a functional block diagram of the apparatus 600, 700 for sensing an abnormality of a breast implant according to some embodiments of the present disclosure.

As shown in FIG. 9, the apparatus 600, 700 according to some embodiments of the present disclosure a wireless power transmitting unit 910 for transmitting a power in a wireless manner to the sensor modules 300 of the patches 200, 400 included in the breast implant 110, an abnormality sensing unit 920 for receiving the pressure signal from at least one of the sensor modules 300 and sensing an abnormality of the breast implant 110 based on the pressure signal, and an alarm generating unit 930 for, upon the abnormality sensing unit 920 sensing the abnormality of the breast implant 110, generating an alarm to the outside.

In some embodiments of the present disclosure, the abnormality sensing unit 920 stores, in a memory (not shown), an initial pressure sensed by each of the sensor modules 300 when the breast implant 110 is inserted in the breast 100, compares pressures indicated by the pressure signals received from the sensor modules 300 with the initial pressures, respectively, and senses the abnormality of the breast implant 110 based on a result of the comparison. For example, when a difference between the pressure indicated the pressure signal received from the sensor module 300 and the initial pressure exceeds a predetermined value (threshold), the abnormality sensing unit 920 determines the abnormality of the breast implant 110.

In some embodiments of the present disclosure, upon the abnormality sensing unit 920 sensing the abnormality of the breast implant 110, the alarm generating unit 930 generates an alarm by means of video or audio signals that can be recognized by the user.

That is, upon the abnormality sensing unit 920 sensing the abnormality of the breast implant 110, the alarm generating unit 930 visually notifies the user of the abnormality of the breast implant 110 through a display (not shown) and acoustically notifies the user of the abnormality of the breast implant 110 through an alarm sound.

A breast implant including a sensor module (a pressure sensor) can be manufactured as follows.

FIGS. 10 to 13 are flowcharts for explaining a method of manufacturing a breast implant according to some embodiments of the present disclosure.

Figure 10:
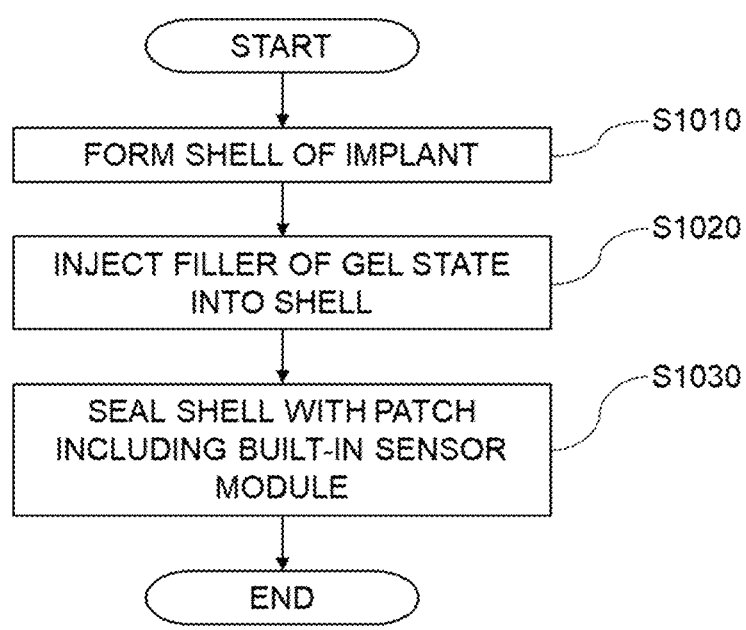

In the example shown in FIG. 10, the method of manufacturing the breast implant according to some embodiments of the present disclosure includes a step of forming a shell of the breast implant including an injection hole for injecting a filler (Step S1010), a step of injecting the filler of the gel state into the shell through the injection hole (Step S1020), and after injecting the filler in the shell, sealing the injection hole with a patch including a first barrier, a second barrier facing the first barrier, and a sensor module between the first barrier and the second barrier, in a manner that the first barrier faces inside the shell and the second barrier faces outside the shell (Step S1030).

Figure 11:
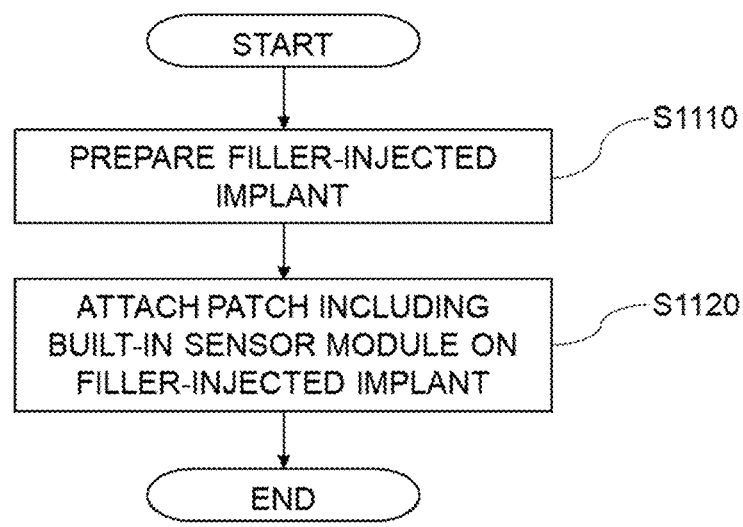

In the example shown in FIG. 11, the method of manufacturing the breast implant according to some embodiments of the present disclosure includes a step of preparing a breast implant including a shell filled with a filler (Step S1110) and a step of attaching a patch including a first barrier, a second barrier facing the first barrier, and a sensor module on the outer surface of the first barrier or between the first barrier and the second barrier, in a manner that the first barrier faces the outer surface of the shell (Step S1120).

Figure 12:
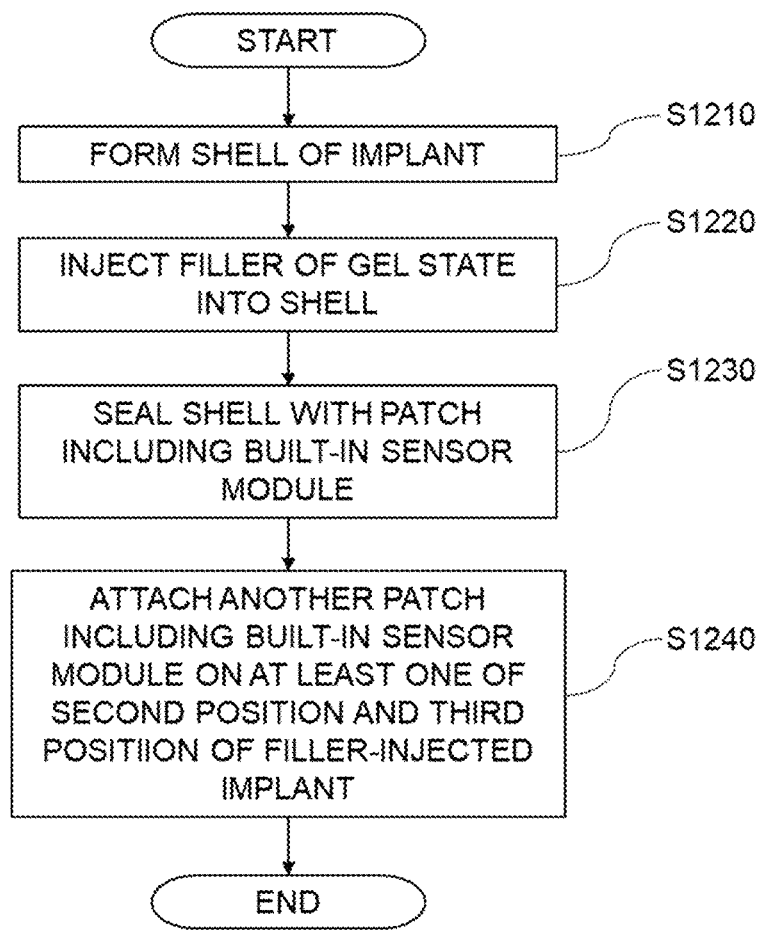

In the example shown in FIG. 12, the method of manufacturing the breast implant according to some embodiments of the present disclosure includes a step of forming a shell of the breast implant including an injection hole for injecting a filler (Step S1210), a step of injecting the filler of the gel state into the shell through the injection hole (Step S1220), after injecting the filler in the shell, sealing the injection hole with a patch including a first barrier, a second barrier facing the first barrier, and a sensor module between the first barrier and the second barrier, in a manner that the first barrier faces inside the shell and the second barrier faces outside the shell (Step S1230), and a step of attaching a patch including a sensor module on at least one of the second position and the third position (Step S1240).

In the example shown in FIG. 13, the method of manufacturing the breast implant according to some embodiments of the present disclosure includes a step of preparing a breast implant including a shell filled with a filler (Step S1310), a step of attaching a patch including a first barrier, a second barrier facing the first barrier, and a sensor module on the outer surface of the first barrier or between the first barrier and the second barrier, in a manner that the first barrier faces the outer surface of the shell (Step S1320), and a step of attaching a patch including a sensor module on at least one of the second position and the third position (Step S1330).

In the methods of manufacturing a breast implant as described above, the sensor module includes at least one pressure sensor for sensing a pressure and outputting a pressure signal, a controller for transmitting the pressure signal from the at least one pressure sensor, and a wireless power receiving unit for receiving a power in a wireless manner from an external device and providing the power to the controller.

In the methods of manufacturing a breast implant as described above, the sensor module further includes a battery for storing the power received by the wireless power receiving unit in a wireless manner.

In this manner, the breast implant according to some embodiments of the present disclosure monitors the pressure applied to the breast implant by means of a sensor tag of a body insertion type including a battery or a sensor tag of a batteryless body insertion type, and when a change of the pressure exceeds a threshold, transmits a signal notifying an abnormality to the apparatus for sensing an abnormality of a breast implant.

For example, the wireless communication and the wireless power transmission and reception can be realized by adding a function of the magnetic resonant coupling to an ultra-high frequency (UHF) RFID communication device or using a near field communication (NFC) method.

As described above, according to some embodiments of the present disclosure, it is possible to provide a breast implant including a sensor-equipped patch with which an abnormality of the breast implant can be effectively sensed after inserting the breast implant in a breast.

Further, according to some embodiments of the present disclosure, it is possible to provide an apparatus for sensing an abnormality of a breast implant, which can effectively sense an abnormality of the breast implant after inserting the breast implant in a breast.

Moreover, according to some embodiments of the present disclosure, it is possible to provide a method of manufacturing a breast implant including a sensor-equipped patch with which an abnormality of the breast implant can be effectively sensed after inserting the breast implant in a breast.

The present disclosure should not be limited to these embodiments but various changes and modifications are made by one ordinarily skilled in the art within the subject matter, the spirit and scope of the present disclosure as hereinafter claimed. Specific terms used in this disclosure and drawings are used for illustrative purposes and not to be considered as limitations of the present disclosure. Exemplary embodiments of the present disclosure have been described for the sake of brevity and clarity. Accordingly, one of ordinary skill would understand the scope of the claimed invention is not to be limited by the explicitly described above embodiments but by the claims and equivalents thereof.

What is claimed is:

1. A breast implant, comprising:
    a shell including an injection hole and forming an outer cover of the breast implant;
    a filler of a gel state injected into the shell through the injection hole;
    a first patch configured to be attached at a first position and to seal the injection hole, the first patch including a first sensor module; and
    a second patch configured to be attached on at least one of (i) a second position opposite of the first position and (ii) a third position to which a pressure due to a gravity is applied when the breast implant is inserted in a breast and a body is kept upright without an external pressure applied, the second patch including a second sensor module separate from the first sensor module;
    wherein the first sensor module is configured to sense a pressure exerted on the breast implant between the filler and the body, and the second sensor module is configured to sense a pressure exerted on the breast implant from either outside of the body or due to gravity.

2. The breast implant according to claim 1, wherein each of the first patch and the second patch includes:
    a first barrier forming a first side facing inside the breast implant;
    a second barrier facing the first barrier and forming a second side opposite to the first side; and
    a sensor module disposed on the first side or between the first barrier and the second barrier, and wherein each of the first sensor module and the second sensor module includes:
        at least one pressure sensor configured to sense a pressure and to output a pressure signal;
        a controller configured to transmit the pressure signal from the at least one pressure sensor; and
        a wireless power receiving unit configured to receive a power in a wireless manner from an external device and to provide the power to the controller.

3. The breast implant according to claim 1, wherein a diameter of the second patch is smaller than a size of the first patch.

4. The breast implant according to claim 1, wherein when the breast implant is inserted in the breast and the body is kept upright without an external pressure applied:
    the first sensor module is configured to sense a pressure exerted on the breast implant between the filler and the body,
    the second sensor module attached on the second position is configured to sense a pressure exerted on the breast implant from outside the body, and
    the second sensor module attached on the third position is configured to sense a pressure exerted on the breast implant due to the gravity.

5. The breast implant according to claim 1, wherein the second patch is attached on an outer surface of the shell with the filler injected in a manner that the first barrier makes contact with the outer surface of the shell.

6. An apparatus for sensing an abnormality of a breast implant, the apparatus comprising:
    a wireless power transmitting unit configured to transmit a power in a wireless manner;
    an abnormality sensing unit configured to receive a pressure signal from at least one of the first sensor module and the second sensor module of the breast implant according to claim 1 and to sense an abnormality of the breast implant based on the pressure signal; and
    an alarm generating unit configured to, upon the abnormality sensing unit sensing the abnormality of the breast implant, generate an alarm.

7. The apparatus according to claim 6, wherein the abnormality sensing unit is configured to store, in a memory, an initial pressure sensed by the first sensor module and the second sensor module when the breast implant is inserted in the body, to compare pressures indicated by the pressure signals received from the first sensor module and the second sensor module with the initial pressure, and to sense the abnormality of the breast implant based on a result of comparison.

8. The apparatus according to claim 6, wherein a threshold for determining the abnormality of the breast implant for at least one of the first sensor module and the second sensor module is set to be larger than that of other sensor modules.

9. The apparatus according to claim 6, wherein thresholds for determining the abnormality of the breast implant for the first sensor module and the second sensor module are set to be different from each other.

10. The breast implant according to claim 1, further comprising:
    a third patch configured to be attached at the third position, the third patch including a third sensor module separate from the first and second sensor modules;
    wherein the second patch is configured to be attached at the second position opposite of the first position, wherein the second sensor module is configured to sense the pressure exerted on the breast implant from outside of the body, and wherein the third sensor module is configured to sense the pressure exerted on the breast implant due to gravity.

* * * * *